(12) United States Patent
Hatlestad

(10) Patent No.: US 8,496,596 B2
(45) Date of Patent: Jul. 30, 2013

(54) SYSTEMS AND METHODS FOR DETERMINING RESPIRATION METRICS

(75) Inventor: John D. Hatlestad, Maplewood, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 755 days.

(21) Appl. No.: 12/700,881

(22) Filed: Feb. 5, 2010

(65) Prior Publication Data
US 2010/0137730 A1 Jun. 3, 2010

Related U.S. Application Data

(62) Division of application No. 11/300,675, filed on Dec. 14, 2005, now Pat. No. 7,662,105.

(51) Int. Cl.
A61B 5/08 (2006.01)

(52) U.S. Cl.
USPC .......................................... 600/529; 600/484

(58) Field of Classification Search
USPC .................................................. 600/529, 484
See application file for complete search history.

(56) References Cited

U.S. PATENT DOCUMENTS

| 4,562,841 A | 1/1986 | Brockway et al. |
| 4,697,591 A | 10/1987 | Lekholm et al. |
| 4,928,688 A | 5/1990 | Mower |
| 5,036,849 A | 8/1991 | Hauck et al. |
| 5,063,927 A | 11/1991 | Webb et al. |
| 5,133,353 A | 7/1992 | Hauser |
| 5,179,945 A | 1/1993 | Van Hofwegen et al. |
| 5,203,348 A | 4/1993 | Dahl et al. |
| 5,230,337 A | 7/1993 | Dahl et al. |
| 5,271,395 A | 12/1993 | Wahlstrand et al. |
| 5,284,136 A | 2/1994 | Hauck et al. |
| 5,301,677 A | 4/1994 | Hsung |
| 5,313,953 A | 5/1994 | Yomtov et al. |

(Continued)

FOREIGN PATENT DOCUMENTS

| EP | 1151719 | 7/2001 |
| EP | 1177764 | 6/2002 |

(Continued)

OTHER PUBLICATIONS

International Search Report and Written Opinion from International Application No. PCT/US2010/036386 dated Oct. 3, 2010, 16 pages.

(Continued)

Primary Examiner — Navin Natnithithadha
Assistant Examiner — Etsub Berhanu
(74) Attorney, Agent, or Firm — Seager, Tufte & Wickhem LLC

(57) ABSTRACT

Systems, devices and methods provide for acquiring respiration information. A respiration information device includes timer circuitry to time a plurality of shorter time apertures and a plurality of longer time apertures. A respiration sensor, which may be implemented as a transthoracic impedance sensor, is configured to generate a signal indicative of patient respiration. For each aperture of the plurality of shorter time apertures and for each aperture of the plurality of longer time apertures, an estimated characteristic of the respiration is determined. Respiration metrics are developed using one or both of the estimated respiration characteristics of the shorter time apertures and the estimated respiration characteristics of the longer time apertures.

20 Claims, 10 Drawing Sheets

U.S. PATENT DOCUMENTS

| | | | |
|---|---|---|---|
| 5,314,459 A | 5/1994 | Swanson et al. |
| 5,318,597 A | 6/1994 | Hauck et al. |
| 5,334,222 A | 8/1994 | Salo et al. |
| 5,360,442 A | 11/1994 | Dahl et al. |
| 5,366,496 A | 11/1994 | Dahl et al. |
| 5,372,606 A | 12/1994 | Lang et al. |
| 5,376,106 A | 12/1994 | Stahmann et al. |
| 5,388,578 A | 2/1995 | Yomtov et al. |
| 5,391,200 A | 2/1995 | KenKnight et al. |
| 5,397,342 A | 3/1995 | Heil, Jr. et al. |
| 5,411,031 A | 5/1995 | Yomtov |
| 5,411,525 A | 5/1995 | Swanson et al. |
| 5,468,254 A | 11/1995 | Hahn et al. |
| 5,540,727 A | 7/1996 | Tockman et al. |
| 5,545,202 A | 8/1996 | Dahl et al. |
| 5,593,431 A | 1/1997 | Sheldon |
| 5,603,732 A | 2/1997 | Dahl et al. |
| 5,620,466 A | 4/1997 | Haefner et al. |
| 5,634,938 A | 6/1997 | Swanson et al. |
| 5,662,688 A | 9/1997 | Haefner et al. |
| 5,697,953 A | 12/1997 | Kroll et al. |
| 5,836,987 A | 11/1998 | Baumann et al. |
| 5,876,353 A | 3/1999 | Riff |
| 5,916,243 A | 6/1999 | KenKnight et al. |
| 5,957,861 A | 9/1999 | Combs et al. |
| 5,974,340 A | 10/1999 | Kadhiresan |
| 5,974,349 A | 10/1999 | Levine |
| 6,026,320 A | 2/2000 | Carlson et al. |
| 6,044,297 A | 3/2000 | Sheldon et al. |
| 6,044,298 A | 3/2000 | Salo et al. |
| 6,055,454 A | 4/2000 | Heemels |
| 6,076,015 A | 6/2000 | Hartley et al. |
| 6,162,183 A | 12/2000 | Hoover |
| 6,221,011 B1 | 4/2001 | Bardy |
| 6,270,457 B1 | 8/2001 | Bardy |
| 6,275,727 B1 | 8/2001 | Hopper et al. |
| 6,277,072 B1 | 8/2001 | Bardy |
| 6,280,380 B1 | 8/2001 | Bardy |
| 6,285,907 B1 | 9/2001 | Kramer et al. |
| 6,312,378 B1 | 11/2001 | Bardy |
| 6,336,903 B1 | 1/2002 | Bardy |
| 6,358,203 B2 | 3/2002 | Bardy |
| 6,360,127 B1 | 3/2002 | Ding et al. |
| 6,368,284 B1 | 4/2002 | Bardy |
| 6,371,922 B1 | 4/2002 | Baumann et al. |
| 6,398,728 B1 | 6/2002 | Bardy |
| 6,409,675 B1 | 6/2002 | Turcott |
| 6,411,848 B2 | 6/2002 | Kramer et al. |
| 6,424,865 B1 | 7/2002 | Ding |
| 6,438,407 B1 | 8/2002 | Ousdigian et al. |
| 6,438,410 B2 | 8/2002 | Hsu et al. |
| 6,440,066 B1 | 8/2002 | Bardy |
| 6,449,509 B1 | 9/2002 | Park et al. |
| 6,454,719 B1 | 9/2002 | Greenhut |
| 6,459,929 B1 | 10/2002 | Hopper et al. |
| 6,480,733 B1 | 11/2002 | Turcott |
| 6,513,532 B2 | 2/2003 | Mault et al. |
| 6,527,729 B1 | 3/2003 | Turcott |
| 6,542,775 B2 | 4/2003 | Ding et al. |
| 6,564,106 B2 | 5/2003 | Guck et al. |
| 6,572,557 B2 | 6/2003 | Tchou et al. |
| 6,589,188 B1 | 7/2003 | Street et al. |
| 6,597,951 B2 | 7/2003 | Kramer et al. |
| 6,600,949 B1 | 7/2003 | Turcott |
| 6,641,542 B2 | 11/2003 | Cho et al. |
| 6,658,292 B2 | 12/2003 | Kroll et al. |
| 6,666,826 B2 | 12/2003 | Salo et al. |
| 6,705,990 B1 | 3/2004 | Gallant et al. |
| 6,708,058 B2 | 3/2004 | Kim et al. |
| 6,741,885 B1 | 5/2004 | Park et al. |
| 6,752,765 B1 | 6/2004 | Jensen et al. |
| 6,773,404 B2 | 8/2004 | Poezevera et al. |
| 6,830,548 B2 | 12/2004 | Bonnet et al. |
| 6,832,113 B2 | 12/2004 | Belalcazar |
| 6,856,829 B2 | 2/2005 | Ohsaki et al. |
| 6,922,587 B2 | 7/2005 | Weinberg |
| 6,993,389 B2 | 1/2006 | Ding |
| 7,013,176 B2 | 3/2006 | Ding |
| 7,020,521 B1 | 3/2006 | Brewer et al. |
| 7,041,061 B2 | 5/2006 | Kramer |
| 7,096,064 B2 | 8/2006 | Deno et al. |
| 7,113,823 B2 | 9/2006 | Yonce et al. |
| 7,115,096 B2 | 10/2006 | Siejko |
| 7,127,290 B2 | 10/2006 | Girouard |
| 7,158,830 B2 | 1/2007 | Yu |
| 7,181,285 B2 | 2/2007 | Lindh |
| 7,206,634 B2 | 4/2007 | Ding |
| 7,228,174 B2 | 6/2007 | Burnes |
| 7,306,564 B2 | 12/2007 | Nakatani et al. |
| 7,310,554 B2 | 12/2007 | Kramer |
| 7,343,199 B2 | 3/2008 | Hatlestad |
| 7,376,457 B2 | 5/2008 | Ross |
| 7,389,141 B2 | 6/2008 | Hall |
| 7,409,244 B2 | 8/2008 | Salo |
| 7,435,221 B1 | 10/2008 | Bharmi et al. |
| 7,468,032 B2 | 12/2008 | Stahmann et al. |
| 7,480,528 B2 | 1/2009 | Brockway et al. |
| 7,483,743 B2 | 1/2009 | Mann et al. |
| 7,499,750 B2 | 3/2009 | Haefner et al. |
| 7,572,225 B2 | 8/2009 | Stahmann et al. |
| 7,606,617 B2 | 10/2009 | Waruar |
| 7,662,105 B2 | 2/2010 | Hatlestad |
| 7,680,534 B2 | 3/2010 | Hopper et al. |
| 1,278,777 A1 | 5/2010 | Zhang et al. |
| 1,278,778 A1 | 5/2010 | Zhang et al. |
| 7,803,118 B2 | 9/2010 | Reisfeld et al. |
| 2004/0049235 A1 | 3/2004 | Deno et al. |
| 2004/0116819 A1 | 6/2004 | Alt |
| 2004/0122294 A1 | 6/2004 | Hatlestad et al. |
| 2004/0127792 A1 | 7/2004 | Siejko |
| 2004/0133079 A1 | 7/2004 | Mazar et al. |
| 2004/0230230 A1 | 11/2004 | Lindstrom |
| 2004/0230243 A1 | 11/2004 | Haefner |
| 2005/0085738 A1 | 4/2005 | Stahmann et al. |
| 2005/0137629 A1 | 6/2005 | Dyjach et al. |
| 2006/0241708 A1* | 10/2006 | Boute ............................ 607/17 |
| 2007/0055115 A1 | 3/2007 | Kwok et al. |
| 2007/0073168 A1 | 3/2007 | Zhang et al. |
| 2007/0118183 A1 | 5/2007 | Gelfand et al. |
| 2007/0149862 A1 | 6/2007 | Pipke |
| 2007/0191697 A1 | 8/2007 | Lynn et al. |
| 2008/0114219 A1 | 5/2008 | Zhang |
| 2008/0162182 A1 | 7/2008 | Cazares et al. |
| 2008/0262360 A1 | 10/2008 | Dalal et al. |
| 2009/0234240 A1 | 9/2009 | Kuenzler |
| 2009/0324034 A1 | 12/2009 | Watson |
| 2010/0073170 A1 | 3/2010 | Siejko et al. |

FOREIGN PATENT DOCUMENTS

| | | |
|---|---|---|
| WO | WO9833553 | 6/1998 |
| WO | WO0240096 | 5/2002 |
| WO | WO03075744 | 9/2003 |
| WO | WO2004062485 | 7/2004 |
| WO | WO2005028029 | 3/2005 |
| WO | WO2008085309 | 7/2008 |

OTHER PUBLICATIONS

File history for U.S. Appl. No. 11/300,675.

Dictionary.com, Definition of window, printed from internet Apr. 12, 2009, 11 pages.

Altshule et al., The Effect of Position on Periodic Breathing in Chronic Cardiac Decomposition, New Eng. Journal of Med., vol. 259, No. 22, pp. 1064-1066, Nov. 27, 1958.

Butler et al., Beta-Blocker Use and Outcomes Among Hospitalized Heart Failure Patients, Journal of the American College of Cardiology, vol. 47, No. 12, 2006, pp. 2462-2469.

Dark et al., Breathing Pattern Abnormalities and Arterial Oxygen Desaturation During Sleep in the Congestive Heart Failure Syndrome, Chest, Jun. 1987, 6:833-6. Abstract only.

Dimopolou I, et al., Pattern of Breathing during Progressive Exercise in Chronic Heart Failure, IJC 81, 2001, 117-121. Abstract Only.

Duguet et al., "Expiratory Flow Limitation as a Determinant of Orthopnea in Acute Left Heart Failure", Journal of the American College of Cardiology, vol. 35, No. 3, 2000, pp. 690-700.

Hoffman et al., Cheyne-Stokes Respiration in Patients Recovering from Acute Cardiogenic Pulmonary Edema, Chest 1990, 97:410-12. Abstract only.

Junyu et al., Posture Detection Algorithm Using Multi Axis DC-Accelerometer, Pace vol. 22, Apr. 1999.

Lee et al., JAMA, 2003, 290:2581-87, Predicting Mortality Among Patients Hospitalized for Heart Failure, derivation and validation of a clinical model. Abstract Only.

Rame et al., "Outcomes after emergency department discharge with a primary diagnosis of heart failure", American Heart Journal, vol. 142(4), Oct. 2001, pp. 714-719.

Rees et al., Paroxysmal Nocturnal Dyspnoea and Periodic Respiration, The Lancet, Dec. 22-29, 1979, pp. 1315-1317. Abstract Only.

Solin et al., Effects of Cardiac Dysfunction on Non-Hypercapnic Central Sleep Apnea, Department of Respiratory Medicine, Alfred Hospital, and Department of Medicine, Monash University Medical School, Melbourne, Victoria, Australia, Apr. 10, 1997, pp. 104-110.

Tkacova et al., Left Ventricular Volume in Patients with Heart Failure and Cheyne-Strokes Respiration during Sleep, Am. Journal, Respir. Crit. Care Med., vol. 156, pp. 1549-1555, 1997.

File History for EP Application No. 10721084.1 as retrieved from European Patent Office System on Aug. 15, 2012, 43 pages.

* cited by examiner

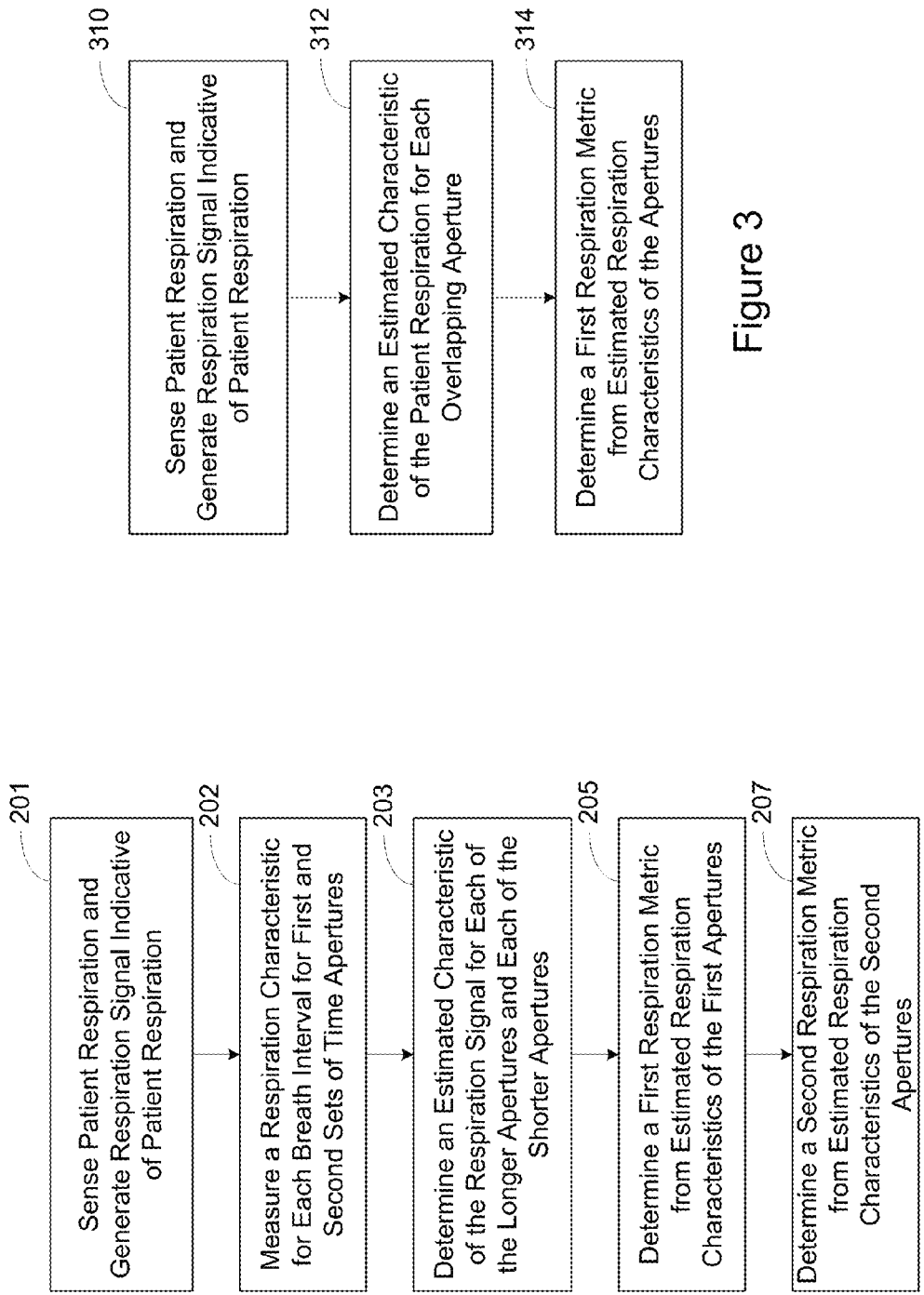

SYSTEMS AND METHODS FOR DETERMINING RESPIRATION METRICS

RELATED PATENT DOCUMENTS

This application is a divisional of U.S. patent application Ser. No. 11/300,675 filed on Dec. 14, 2005, which is incorporated herein by reference in its entirety.

FIELD OF THE INVENTION

The present invention relates generally to respiration detection and monitoring and, more particularly, to generating respiration metrics.

BACKGROUND OF THE INVENTION

The human body functions through a number of interdependent physiological systems controlled through various mechanical, electrical, and chemical processes. The metabolic state of the body is constantly changing. For example, as exercise level increases, the body consumes more oxygen and gives off more carbon dioxide. The cardiac and pulmonary systems maintain appropriate blood gas levels by making adjustments that bring more oxygen into the system and dispel more carbon dioxide. The cardiovascular system transports blood gases to and from the body tissues. The respiratory system, through the breathing mechanism, performs the function of exchanging these gases with the external environment. Together, the cardiac and respiratory systems form a larger anatomical and functional unit denoted the cardiopulmonary system.

Various disorders that affect the cardiovascular system may also impact respiration. For example, heart failure is an abnormality of cardiac function that causes cardiac output to fall below a level adequate to meet the metabolic demand of peripheral tissues. Heart failure is usually referred to as congestive heart failure (CHF) due to the accompanying venous and pulmonary congestion. Congestive heart failure may have a variety of underlying causes, including ischemic heart disease (coronary artery disease), hypertension (high blood pressure), and diabetes, among others.

Various types of disordered respiration are associated with CHF. For example, rapid shallow breathing is one of the cardinal signs of heart failure. The appearance of rapid, shallow breathing in a CHF patient is often secondary to increased pulmonary edema, and can indicate a worsening of patient status. An abnormally high respiration rate thus can be an indicator of CHF decompensation. It is estimated that nearly one million hospital admissions for acute decompensated congestive heart failure (CHF) occur in the United States each year, which is almost double the number admitted 15 years ago. The re-hospitalization rates during the 6 months following discharge are as much at 50%. Nearly 2% of all hospital admissions in the United States are for decompensated CHF patients, and heart failure is the most frequent cause of hospitalization in patients older than 65 years. The average duration of hospitalization is about 6 days. Despite aggressive therapies, hospital admissions for CHF continue to increase, reflecting the prevalence of this malady.

Because of the complex interactions between the cardiovascular, pulmonary, and other physiological systems, as well as the need for early detection of various diseases and disorders, an effective approach to monitoring and early diagnosis is needed. Accurately characterizing patient respiration aids in monitoring and diagnosing respiration-related diseases or disorders. Evaluating patient respiration information may allow an early intervention, preventing serious decompensation and hospitalization.

SUMMARY OF THE INVENTION

The present invention is directed to methods, devices, and systems providing respiration information. One embodiment is directed to a method for providing respiration information. The method involves generating a signal indicative of respiration. For each apertures of a plurality of shorter time apertures and for each aperture of a plurality of longer time apertures an estimated characteristic of the respiration is determined based on the respiration signal. One or more respiration metrics are determined using one or both of the estimated respiration characteristics of the plurality of shorter time apertures and the estimated respiration characteristics of the plurality of longer time apertures. In some configurations, at least one of generating the signal, determining the estimated characteristic, and determining the one or more respiration metrics is performed at least in part implantably.

According to one implementation of the method, determining the estimated respiration characteristic for each aperture includes measuring a respiration characteristic for each breath cycle of the aperture. The estimated respiration characteristic for the aperture is determined based on the measured respiration characteristics. For example, the estimated respiration characteristic for each of the apertures may be based on a median value of the measured respiration characteristics. Determining the estimated respiration characteristic for each aperture may involve determining an estimated respiration rate for each aperture.

The estimated respiration characteristic for each of the plurality of shorter time apertures may be a maximum respiration rate for each of the plurality of shorter time apertures. The estimated respiration characteristic for each of the plurality of longer time apertures may be a minimum respiration rate for each of the plurality of longer time apertures. The respiration metrics may be a daily maximum respiration rate determined using the maximum respiration rates of the plurality of shorter time apertures and a daily minimum respiration rate determining using the minimum respiration rates of the plurality of longer time apertures.

The method may also involve developing a trend using at least one of the estimated respiration characteristics determined for the plurality of shorter time apertures, the estimated respiration characteristics determined for the plurality of longer time apertures, and the one or more respiration metrics.

The method may also involve detecting a presence of a disease or disorder using at least one of the estimated respiration characteristics determined for the plurality of shorter time apertures, the estimated respiration characteristics determined for the plurality of longer time apertures, and the one or more respiration metrics. For example, the disease or disorder detected may include heart failure and/or a symptom or heart failure. The method may include a progression of heart failure and/or a heart failure symptom using at least one of the estimated respiration characteristics determined for the plurality of shorter time apertures, the estimated respiration characteristics determined for the plurality of longer time apertures, and the one or more respiration metrics. A therapy may be initiated, modified or terminated based on the heart failure progression. According to one implementation, the therapy includes a cardiac pacing therapy.

Another embodiment of the invention is directed to a respiration information device. The respiration information device includes timer circuitry configured to time a plurality of shorter time apertures and a plurality of longer time apertures. A respiration sensor, which may be implemented as a transthoracic impedance sensor, is configured to generate a signal indicative of patient respiration. Respiration information circuitry determines, for each aperture of the plurality of shorter time apertures and for each aperture of the plurality of longer time apertures, an estimated characteristic of the respiration. The respiration information circuitry may also be configured to determine one or more respiration metrics using one or both of the estimated respiration characteristics of the shorter time apertures and the estimated respiration characteristics of the longer time apertures. In some embodiments, at least one of the timer circuitry, the respiration sensor, and the respiration information circuitry includes an implantable component.

In one implementation, the respiration information circuitry includes measurement circuitry configured to measure a respiration rate for each breath cycle of each aperture. A respiration processor is coupled to the measurement circuitry and is configured to determine an estimated respiration rate for each aperture based on the measured respiration rates. For example, the respiration information circuitry may be configured to determine a maximum respiration rate from the estimated respiration rates of the plurality of shorter time apertures and to determine a minimum respiration rate from the estimated respiration rates of the plurality of longer time apertures.

The respiration information device may further include a trending unit and/or a diagnostics unit. The trending unit is configured to develop a trend using at least one of the estimated respiration characteristics determined for the plurality of shorter time apertures, the estimated respiration characteristics determined for the plurality of longer time apertures, and the one or more respiration metrics. The diagnostics unit is configured to detect a presence of a disease or disorder, such as heart failure, using at least one of the estimated respiration characteristics determined for the plurality of shorter time apertures, the estimated respiration characteristics determined for the plurality of longer time apertures, and the one or more respiration metrics.

The respiration information device may also include a therapy control unit configure to control a therapy, such as a cardiac pacing therapy, based on a presence of a disease or disorder.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 2 is a flowchart illustrating a method for determining respiration metrics using longer duration apertures to determine a first respiration metric and shorter duration apertures to determine a second respiration in accordance with embodiments of the invention;

FIG. 3 is a flowchart illustrating the use of overlapping apertures to determine respiration metrics is in accordance with further embodiments of the invention;

Figure 1A:
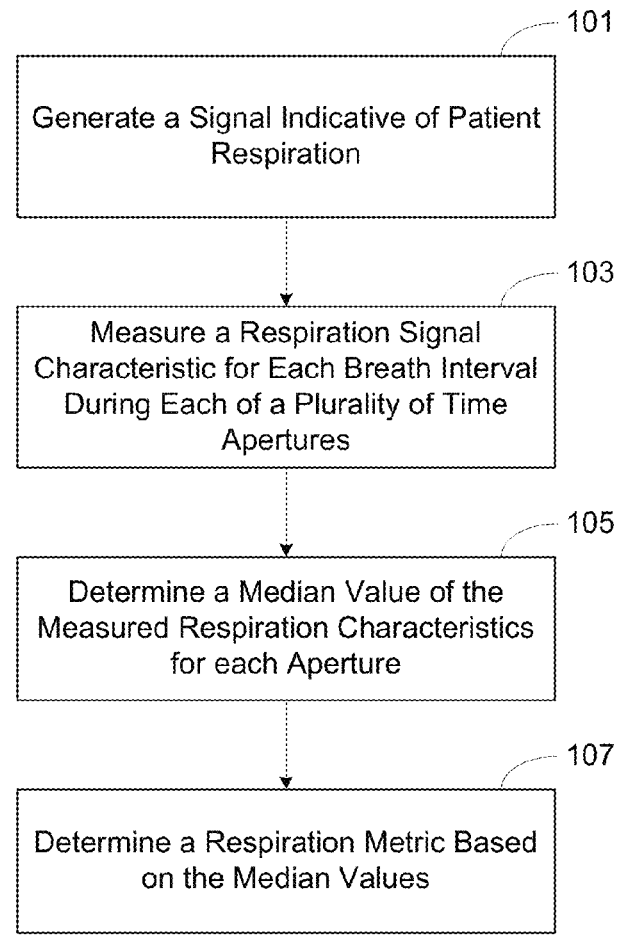
FIG. 1A is a flowchart illustrating the use of median estimators to derive respiration metrics in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

A wide variety of medical devices may be configured to quantify patient respiration in accordance with the present invention. Such devices may be configured with a variety of sensor arrangements for sensing patient respiration, including external respiration sensors, implantable intrathoracic respiration sensors, such as transvenous, endocardial, and/or epicardial sensors (i.e., intrathoracic electrodes), and/or subcutaneous, non-intrathoracic sensors, including can, header, and indifferent electrodes, and subcutaneous arrays or lead electrodes (i.e., non-intrathoracic electrodes). Quantification of patient respiration may be implemented to estimate respiration characteristics, determine respiration metrics and/or develop trends based on the respiration characteristic and/or metrics. The respiration information developed by these devices may be used to develop a respiration trend based on a patient's respiration rate distribution. Such devices are referred to herein generally as a respiration sensing medical device (RSMD) for convenience.

Respiration rate has been shown to be predictive of mortality in a CHF patient population. Symptoms of dyspnea are among the primary reasons for patients' reduced quality of life and are a primary reason why many CHF patients return to the hospital during a CHF decompensation episode. When monitoring or diagnosing CHF patients, patient respiration rate is an important symptom. Respiration rate information yields knowledge of how long a patient stays dyspneic so as to relate to the worsening of their CHF disease state. When the patient spends more time at higher respiration rates, this is indicative of a worsening of their CHF status.

As heart failure patients become acutely decompensated, they may present with tachypnea with abnormally elevated respiration rates of 25-30 breaths per minute, even at rest. Even in the chronic, non-decompensated state, heart failure patients have elevated respiration rates. These rates become even more highly elevated in associated with decompensation. Thus, for many patients, respiration rate provides a valuable indication or prediction of impending acute decompensation of congestive heart failure. Information developed from respiratory rate data in accordance with the present invention provides for enhanced monitoring and therapy management of CHF patients, particularly when the CHF status of a patient is in decline.

Methodologies in accordance with the present invention advantageously provide physicians with a quantified respiration metric and/or trend that can be used to monitor a patient's changing CHF status and quantitatively evaluate the effectiveness of therapy (e.g., drug or cardiac stimulation therapy) delivered to the patient. The methodologies used for developing respiration data involve measuring values of a respiration characteristic, which may be respiration rate, but could also be breath interval, tidal volume, and/or other respiration characteristics. The respiration characteristic measurements may be made for one or more breath cycles, or each breath cycle during a plurality of time apertures, which may or may not be overlapping in time. An estimated respiration characteristic, e.g., estimated rate, breath interval, tidal volume, etc, may be determined from the set of measured characteristic values for a particular aperture to summarize the measurements for the particular aperture. In one implementation, the median value of the respiration characteristic measurements made during an aperture is used to estimate the respiration characteristic of the aperture. Other statistical estimates (e.g., mean) or non-statistical estimates (e.g., based on measured morphological characteristics of the respiration signal) may alternatively be used. The estimated respiration characteristics of a plurality of apertures may be used to develop a respiration trend, or may be used to derive a respiration metric that spans a period of time, such as a daily minimum value or daily maximum value. The respiration metrics may also be trended. As applied herein, an estimated respiration characteristic is estimated based on the measured respiration characteristic values of an individual aperture. Respiration metrics, such as daily respiration metrics, are determined based on the estimated respiration characteristics of a plurality of apertures.

One implementation involves the use of a median estimator to determine daily respiration rate metrics, such as maximum respiration rate over a period of time and/or daily minimum respiration rate over a period of time. A daily median respiration rate may also be determined. The minimum respiration rate may well be the most specific measure of patient respiratory distress. For example, if during the course of the day, the respiratory rate never drops below 18 breaths/minute, it may indicate an abnormal rapid-shallow breathing pattern, even at rest. This may provide a valuable measure of patient respiratory status, including respiration mode changes associated with heart failure decompensation.

The daily maximum respiration rate may be best interpreted by considering it in association with the patient's daily activity. In a healthy, active patient, the maximum respiration rate will be significantly higher than the minimum value, and will vary considerably from day to day, reflecting the variability in the patient's activities. If elevated maximum respiration rates are associated with periods of very limited activity, the patient may be experiencing exertional dyspnea even at low levels of exertion (for example, simply walking around the house, or climbing the stairs), which may indicate worsening patient status. On the other hand, a person whose activities are severely limited by health conditions may show less of a spread from minimum to maximum, and less day-to-day variability in maximum respiration rate, due to limited, consistent daily activity patterns.

The median respiration rate is representative of the predominant respiration rate for a given time period. The daily median is relatively insensitive to transiently elevated respiration rates during periods of high activity, and also relatively insensitive to the lowest respiration rates typically occurring during deep sleep. The median corresponds closely to the resting respiration rate a physician observes during a clinic visit.

In one embodiment, a patient's daily minimum respiration rate, daily maximum respiration rate, and daily median respiration rate are determined. In this embodiment, the patient's respiration rate is measured for each breath cycle in a plurality of time apertures that cover about a 24 hour period. The median respiration rate is estimated for each time aperture. The daily minimum respiration rate is determined as the minimum median respiration rate of the time apertures spanning the 24 hour period. The daily maximum respiration rate is determined as the maximum median respiration rate of the time apertures spanning the 24 hour period. In one implementation, the daily median respiration rate may be determined as the median of the median respiration rates estimated for all of the time apertures that span the 24 hour period. In another implementation, the daily median respiration rate may be determined as the median value of all the respiration rate values measured over the 24 hour period.

The use of median estimators to derive respiration metrics is illustrated in the flowchart of FIG. 1A. Patient respiration is sensed and a signal indicative of patient respiration is generated 101. The patient respiration signal may be generated, for example, by any of a variety of implantable or patient external sensors, such as an implantable transthoracic impedance sensor, external respiratory bands having piezoelectric or other sensor elements, a respiratory mask flow sensor, or other types of respiration sensors. A characteristic of the respiration signal, such as respiration rate per breath cycle, is measured 103 during each of a plurality of time apertures. The median value of the respiration characteristic measurements for each aperture is determined 105. For example, if respiration rate is the measured characteristic, the median value of the respiration rates measured for each breath cycle during the aperture is determined. The median value is used to estimate the respiration rate of the aperture. One or more respiration metrics are determined 107 based on the estimated respiration rates (i.e., median values) of the apertures.

Figure 1B:
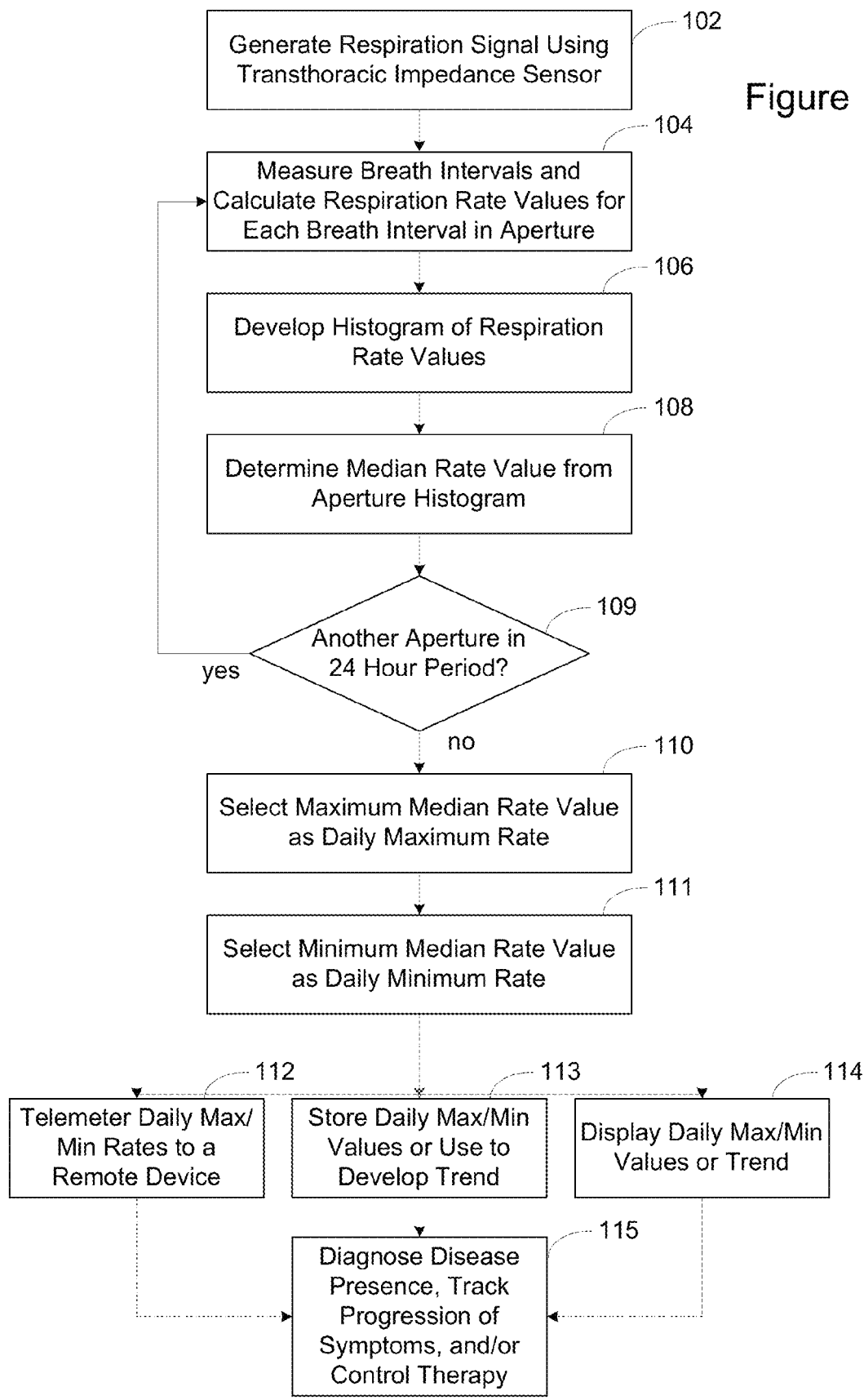
FIG. 1B is a flowchart illustrating a method for generating and using daily respiration metrics in accordance with embodiments of the invention.

In one embodiment, a method for generating and using daily respiration metrics is illustrated in FIG. 1B. The process involves the use of an implantable transthoracic impedance sensor for determining a daily maximum and/or daily minimum respiration metric based on median estimators for the aperture respiration characteristics. In accordance with this embodiment, a respiration signal is generated 102 by an transthoracic impedance sensor implemented in conjunction with an implantable cardiac rhythm management (CRM) device. The transthoracic impedance sensor comprises intracardiac electrodes coupled to sensor drive/sense circuitry disposed within the CRM housing. The sensor drive circuitry delivers an electrical excitation signal, such as a strobed sequence of current pulses or other measurement stimuli, across the thorax via one set of the intracardiac electrodes. In response to the drive current, a response voltage is sensed by the sense circuitry using another set of the intracardiac electrodes. The response voltage represents the transthoracic (i.e., across a portion of the chest or thorax) impedance. Transthoracic impedance sensing provides a voltage signal that tracks patient respiration and may be used to determine how fast and/or how deeply a patient is breathing. Additional aspects of transthoracic impedance sensing that may be utilized in conjunction with various embodiments of the present invention are described in commonly owned U.S. Pat. No. 6,076, 015 which is incorporated herein by reference.

A plurality of time apertures, covering about a 24 hour period, are superimposed relative to the generated respiration signal. The breath intervals occurring in each aperture are measured 104 and respiration rates for each breath cycle are calculated as the inverse of each measured breath interval. A histogram of the measured respiration rates is developed 106. The median value of the measured respiration rates determined from the histogram is computed and stored 108. Median values for each of the apertures are stored 109 throughout the 24 hour period. The maximum of the median values is selected 110 as the maximum daily respiration rate. The minimum of the median values is selected 111 as the minimum daily respiration rate. The daily minimum and maximum respiration rates may optionally be telemetered 112 to a remote device, and/or stored or used 113 to develop trend data within the CRM device or remote device. The daily minimum and/or maximum respiration rates, or trend data developed from the daily metrics, may optionally be displayed 114 on the device programmer screen or other user interface device as individual daily respiration metrics or as trended data. The daily maximum and/or minimum respiration rates or trends of these rates may be used 115 for disease diagnosis and/or to track the progression of disease symptoms and/or to control therapy. Although this example describes the use of daily metrics, other periodic metrics may also be determined, such as weekly metrics, bi-weekly metrics, or monthly metrics. In addition, metrics other than maximum and minimum respiration rates may be determined, such as the daily, weekly, monthly, etc., median or mean respiration rates.

The use of median estimators provides a robust determination of the daily respiration metrics. Breath detection errors may cause extreme values in the breath interval stream which show up as extreme measured respiration rate values in the distribution. The median is inherently less sensitive to extreme values on the tail of the distribution than the mean. Even without detection errors, the breath intervals themselves often form a skewed distribution due to variable respiration patterns within the aperture, such that the median is a more appropriate measure of the central tendency of the respiration intervals within an aperture. While other respiration statistics, such as the mean value, may be used, the median typically provides estimates more representative of the predominant respiration rate for a time aperture than the mean. This is largely due to the frequently asymmetric respiration interval histograms, which may have long "tails" that corrupt the mean estimator. Furthermore, the median lends itself to simple, efficient computation in terms of interval histograms.

In some embodiments, time apertures used to determine one respiration metric may have a different duration than the time apertures used to determine another respiration metric. The duration of the time aperture required to accurately estimate a particular respiration characteristic based on measurements taken within the aperture is related to the frequency of occurrence of the respiration characteristic used to develop the estimate. A statistically stable, consistent estimate requires a sufficiently long observation aperture. Stability of a respiration characteristic estimate improves with increasing aperture duration which allows a corresponding increase in the number of respiration cycles over which to compute the estimated characteristic. Selection of time aperture duration involves a trade-off between the stability of the estimate and the desire to capture transient, relatively short-term changes in respiration characteristics, due to exercise, for example, or other short-term factors.

The flowchart of FIG. 2 illustrates a method for determining respiration metrics using longer duration apertures to determine a first respiration metric and shorter duration apertures to determine a second respiration metric. The example provided in FIG. 2 involves two sets of apertures of different durations which are used to determine first and second respiration metrics, although this process could be extended to any number of aperture sets and respiration metrics.

Patient respiration is sensed 201 and a signal indicative of respiration is generated. Respiration signal characteristic values are measured 202 during each aperture in two sets of time apertures, denoted first and second time apertures, where the apertures of the first set have a longer duration than apertures of the second set. An estimated respiration characteristic for the aperture is estimated 203 from the measured respiration characteristic values for each long aperture and for each short aperture. The estimated respiration characteristics of the first (long) apertures are used to determine 205 a first respiration metric. The estimated respiration characteristics determined for the second (short) apertures are used to determine 207 a second respiration metric.

The processes illustrated by FIG. 2 may be used in developing daily maximum and minimum respiration rate metrics, for example. Ideally, to accurately estimate peak respiration rates, the time aperture should be of a similar duration to the shortest duration episode which is expected to significantly affect the respiration rate estimate for the aperture, so long as this aperture contains enough breaths to provide a reliable estimate of respiration rate. Thus, time apertures used to determine the daily minimum respiration rate may be longer than the time apertures used to determine the daily maximum respiration rate. Because the conditions producing the daily minimum rate, such as sleep, typically last on the order of hours, longer apertures tend to produce quite stable, consistent estimates of the minimum respiration rate metric determined from a number of apertures. In one implementation, longer duration apertures of about 30 minutes may be used to determine the daily minimum respiration metric. At an average resting respiration rate of 15 breaths/minute, there will be an average of 450 breaths per thirty minute aperture. A 30 minute aperture duration will provide good performance for very low respiration rates, providing 120 breaths within the thirty minute aperture on which to base the estimate at a respiration rate of 4 breaths/minute, which is selected as a minimum respiration rate limit in some embodiments. Respiration rates that fall below the minimum respiration rate limit may be discarded and never enter into the computation of respiration metrics or trends.

Conditions producing the daily maximum rate are typically short in duration (e.g. exercise lasting from about 5-60 minutes). Thus, using an unnecessarily long time aperture in estimating the daily maximum rate will lead to underestimation of the peaks, since the breaths within the aperture will be a mixture of those from exercising and resting conditions. For the daily maximum respiration rate metric, the desire to accurately capture relatively short-term changes in respiration rate due to short duration activities of daily living places different requirements on the aperture length.

While it is still desired to have a sufficient number of breaths on which to form a reliable estimate, it is also beneficial to have a short duration aperture so that relatively brief elevations in rate are more accurately estimated. For this reason, a shorter aperture is ideally used in the algorithm to compute the daily maximum rate metrics. Since this aperture will be used only for computation of daily maximum rates, there is less concern that the aperture be long enough to provide enough breaths at the lower extremes of respiration rate, e.g. at about 4 breaths/minute. An aperture duration of about 10 minutes may be chosen for computing the daily maximum respiration rate metrics. This aperture duration will provide good performance for elevated respiration rates with a duration of as low as 5 minutes or less, and for normal respiration rates (even those as low as 10 breaths/minute) will still provide at least 100 breaths within the aperture on which to base the estimate. In some embodiments, a maximum respiration rate is used. For example, the maximum respiration rate may be about 65 breaths/minute. Respiration rates beyond the maximum respiration rate limit may be discarded and never enter into the computation of respiration metrics or trends.

The median value provides a robust estimate of the respiration characteristics of an aperture as long as the sample size is reasonably large. Accordingly, it is natural to require that the median value of a respiration characteristic, such as respiration rate, be determined based on a minimum number of values measured in the aperture. Typically, there should be on the order of about 100 or more samples in the distribution. Thus, even for the lowest allowable respiration rate, a 30 minute aperture contains a sufficient number of breath intervals to form a reasonable estimate of the respiration rate median.

Due to the possibility of missed detections and/or periods of no breathing (apnea), the situation may arise that a respiration characteristic may be estimated using a small number of breath intervals. In order to protect against the possibility of reporting a respiration characteristic of an aperture based on a undesirably small number of respiratory cycles, any characteristic derived using too few breaths may be marked as invalid, and not be used to develop the daily respiration metrics or trends.

Further, due to potential respiration sensor malfunctions, or sensitivity issues, it is conceivable that estimates of a respiration characteristic, such as respiration rate, will be unavailable for a significant portion of the day. If respiration rate estimates are unavailable for too much of the day, then the validity of the respiration metrics, e.g., minimum rate, maximum rate, median rate for that period may be compromised. For example, if less than 18 hours of valid respiration rate estimates exist for a given day, the respiration metrics and/or trend values for that day may be declared invalid, and not be presented to the end user.

Some embodiments of the invention involve generating respiration signals in apertures which are overlapping in time.

The use of overlapping apertures reduces the potential of misestimating the respiration characteristic of an aperture due to a period of temporarily changed characteristics. For example, with respect to respiration rate, even with aperture widths selected to enhance respiration rate characteristic estimation as described above, the potential exists for misestimating an aperture's respiratory rate if a period of elevated or depressed respiratory rate falls on the border between two adjacent time apertures. This will result in two consecutive apertures in which the respiration contains a mixture of "slow" and "fast" intervals, leading to a widened (potentially bimodal) distribution of intervals. The respiration rate estimate is likely to fall short of the respiratory rate excursion, and will likely report a "compromise" respiration rate estimate. In order to ensure that the estimated aperture respiration rates are not erroneous due to this aperture edge effect, it is advantageous to overlap the apertures by a certain amount, such as about 50%. In this configuration, if an event is right on the edge of two adjacent apertures, it will fall in the center of the overlapped aperture.

The use of overlapping apertures to determine respiration metrics is illustrated in the flowchart of FIG. 3. Patient respiration is sensed and a respiration signal is generated 310. A respiration characteristic, e.g., respiration rate, is estimated 312 for each overlapping aperture based on measured rates for each breath cycle of the respiration signal. A respiration metric is determined 314 based on the estimated respiration characteristics of a plurality of apertures. For example, daily respiration metrics, such as a daily maximum respiration rate or daily minimum respiration rate, may be determined based on estimated respiration rate characteristics of a plurality of apertures that cover about a 24 hour period.

As previously discussed, estimation of respiration rate for each aperture may be performed using breath cycles that fall within a minimum rate limit or maximum rate limit. Breath cycles that are beyond the minimum or maximum rate limit may be discarded, and not used to estimate the respiration rate characteristic for the apertures, to determine the respiration rate metrics, or to develop trends based on the respiration rate characteristics or respiration rate metrics.

In accordance with some embodiments, the respiration signal used to estimate the respiration characteristics may be the signal generated by a transthoracic impedance sensor of an implantable rate adaptive pacemaker. The transthoracic impedance signal typically has been filtered by the sensor circuitry to remove components of cardiac activity and other noise from the signal. However, particularly for patients with highly unstable heart rates, such as occur with atrial fibrillation, the filtering designed to remove the cardiac activity component from the transthoracic impedance signal is not always completely effective. At times there may be a considerable amount of cardiac activity component left in the waveform after filtering. These artifacts can cause a significant number of false breath detections leading to erroneously high estimates of respiration rate.

Figure 4:
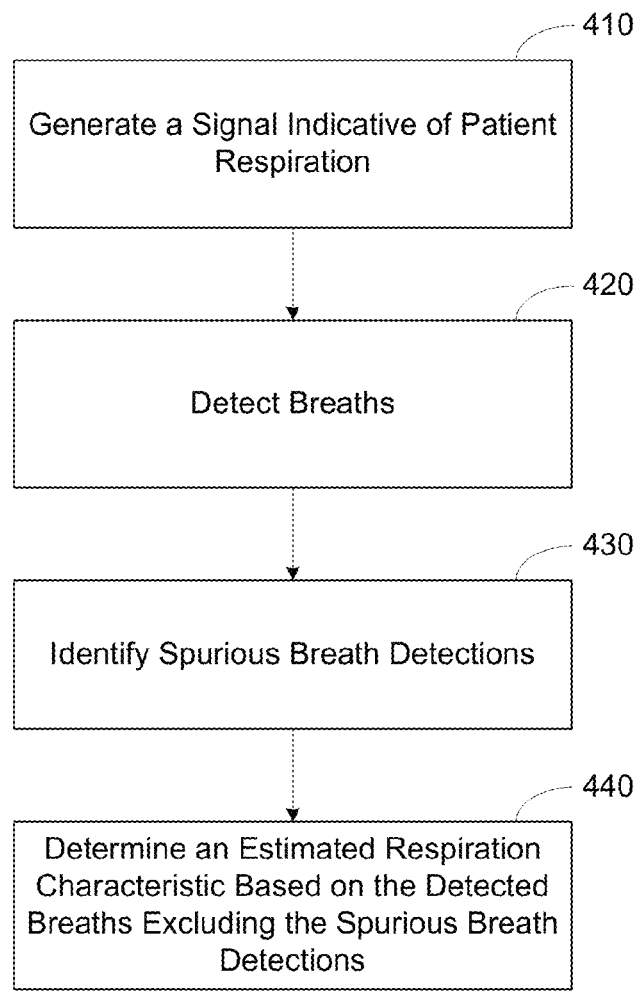
FIG. 4 is a flowchart illustrating a method for removing a predominance of the erroneous breath detections in accordance with other embodiments of the invention.

In accordance with some embodiments of the invention, a "breath pruning" process is implemented to remove a predominance of the erroneous breath detections, such as those triggered by cardiac activity. The process is illustrated by the flowchart of FIG. 4. A signal indicative of patient respiration is generated 410. Breaths are detected 420 from the respiration signal. Spurious breath detections associated with cardiac activity are identified 430. An estimated respiration characteristic is determined 440 based on the detected breaths excluding the spurious breath detections.

Figure 5:
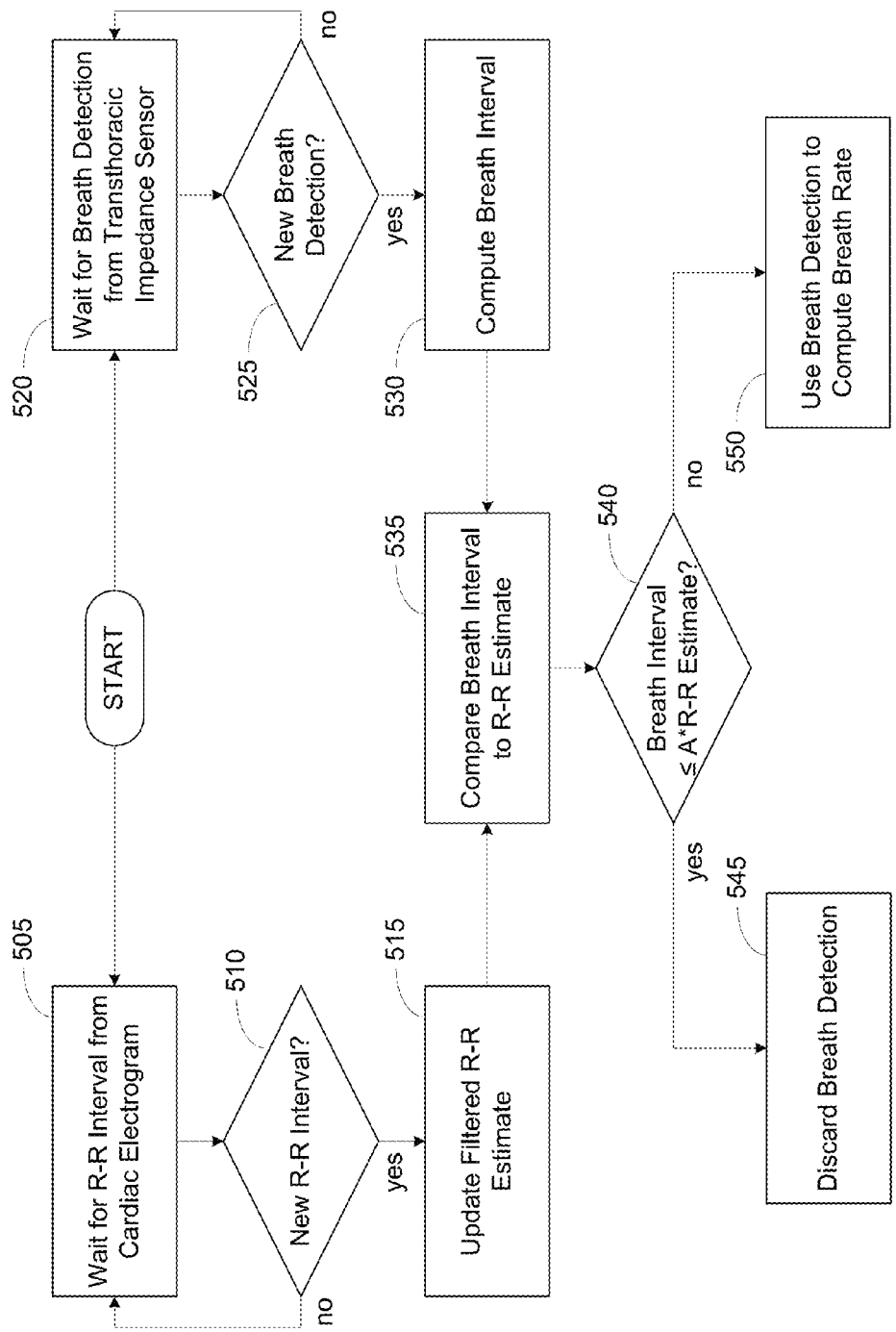
FIG. 5 illustrates a more detailed flowchart of a process for detecting spurious measurements caused by components of cardiac activity in the respiration waveform in accordance with embodiments of the invention.

FIG. 5 illustrates a more detailed flowchart of a process for identifying spurious breath detections caused by components of cardiac activity in the respiration waveform. The process illustrated in FIG. 5 compares breath intervals to a multiple of a cardiac R-R interval estimate to determine whether a breath detection should be used to determine a breath interval and to calculate breath rate. The system waits 505 for a new R-R interval which may be detected, for example, using a cardiac electrogram signal. If a new R-R interval is detected 510, the detected R-R interval is used to update 515 a filtered R-R estimate ($RR_{est}(n)$). In one embodiment, the updated R-R estimate, $RR_{est}(n)$, may be expressed as follows:

$$RR_{est}(n)=31/32*RR_{est}(n-1)+1/32*RR(n) \quad [1]$$

where RR(n) is the current detected R-R interval and $RR_{est}(n-1)$ is the previous filtered R-R estimate.

The system waits 520 for a new breath detection. If a new breath is detected 525, a breath interval is computed 530 by subtracting the last previous valid breath time from the new breath time.

The breath interval is compared 535 to a multiple of the most recently updated filtered R-R interval estimate, $RR_{est}(n)$. If the breath interval is 540 less than the R-R interval estimate, $RR_{est}(n)$, multiplied by a coefficient, such as about 2.15, for example, the new breath detection is discarded 545 and the breath interval computed based on the discarded breath detection is not used to calculate a breath rate. If the breath interval is 540 greater than or equal to $RR_{est}(n)$ multiplied by the coefficient, then the breath rate is computed 550 for the breath interval. For example, the breath rate may be calculated from the breath interval in breaths per minute as follows:

$$\text{Breath Rate}=60/\text{Breath Interval}, \quad [2]$$

where Breath Interval is in units of seconds.

As previously discussed, the breath rates of each breath in an aperture may be used to estimate the breath rate for the aperture. In one implementation, the characteristic breath rate for the aperture is estimated using the median value of all the breath rates measured in the aperture.

Figure 6A:
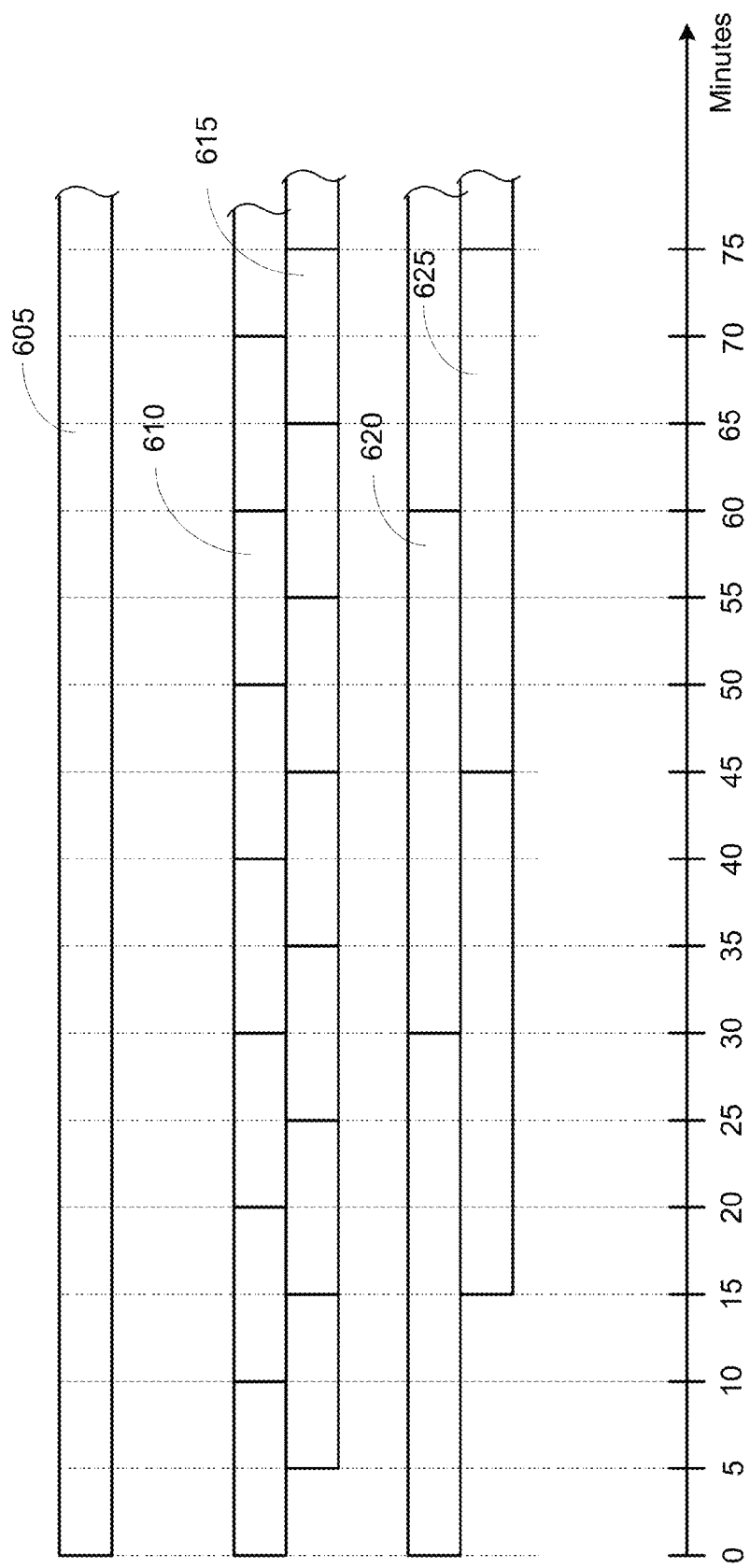
FIGS. 6A and 6B illustrate an implementation for determining respiration metrics including daily minimum respiration rate, daily maximum respiration rate, and daily median respiration rate in accordance with an embodiment of the invention
Figure 6B:
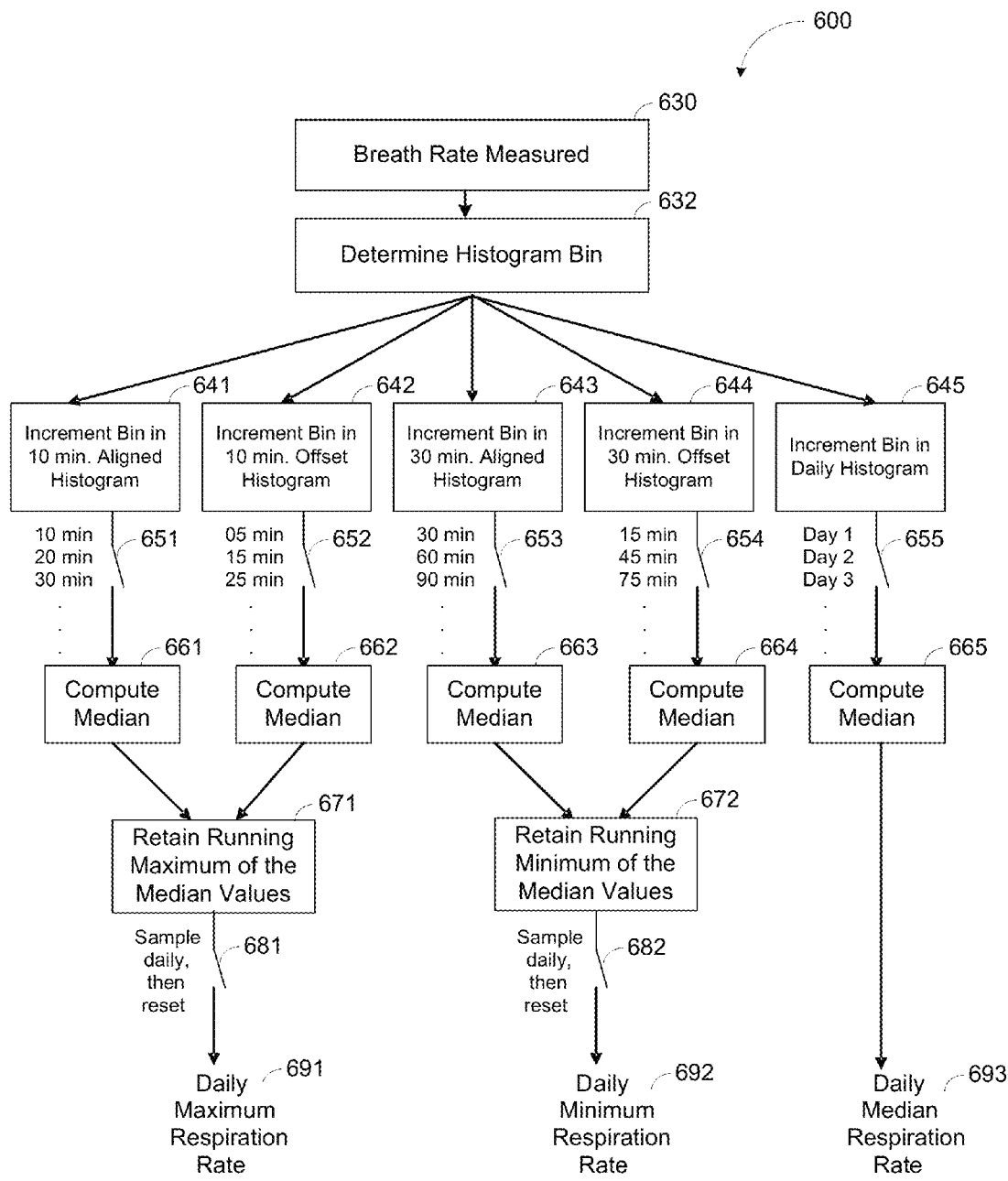

FIGS. 6A and 6B illustrate an implementation for determining respiration metrics including daily minimum respiration rate, daily maximum respiration rate, and daily median respiration rate in accordance with an embodiment of the invention. Patient respiration is sensed and a respiration signal is generated. Overlapping apertures, as illustrated in FIG. 6A, are superimposed on the respiration signal. The apertures include a 24 hour aperture 605 which is used to determine a daily median respiration rate. The apertures also include 10 minute aligned apertures 610 and 10 minute offset apertures 615. The 10 minute offset apertures 615 are offset from the 10 minute aligned apertures 610 by 50%. The 10 minute aligned and offset apertures 610, 615 are used to determine a daily maximum respiration rate. The overlapping apertures also include 30 minute aligned apertures 620 and 30 minute offset apertures 625. The 30 minute offset apertures 625 are offset from the 30 minute aligned apertures 620 by 50%. The 30 minute aligned and offset apertures 620, 625 are used to determine a daily maximum respiration rate.

Breath rates for each respiration cycle are measured and are used to update histograms corresponding to each aperture. In the implementation illustrated in FIGS. 6A and 6B, five concurrently running histograms are used, a 10 minute aligned histogram, a 10 minute offset histogram, a 30 minute aligned histogram, a 30 minute offset histogram, and a 24 hour histogram. A median respiration rate value is determined from each histogram. The daily minimum rate is determined from the median values of the 30 minute aligned and offset histograms that span a 24 hour period. The daily maximum rate is determined from the median values of the 10 minute aligned and offset histograms that span the 24 hour period. The daily median rate is the median value of the 24 hour histogram. A process 600 for determining these daily metrics in accordance with one embodiment is illustrated in FIG. 6B.

Breath rates are measured 630 from the respiration signal and used to update the five concurrently running histograms. The respiration signal may be generated, for example, by a transthoracic impedance sensor signal implemented in an implantable device. Breath detections received from the sensor may be pre-processed as described, for example, in connection with FIGS. 4 and 5, to avoid the use of spurious breath detections in determining the respiration metrics or trends. The process 600 may require that the breath rates meet certain criteria. In addition to providing breath rates for use in the respiration metric process 600, the respiration sensor circuitry, e.g., transthoracic impedance sensor, may provide data quality/status flags. Flags produced by the impedance sensor noise detection hardware/software may be used by the respiration metric process 600 to avoid using potentially corrupted data flagged as too noisy by the sensor. Further, the breath rates used to update the histograms may be constrained to fall within a certain range of breath rates, e.g., about 4 breaths/minute to about 65 breaths/minute.

A histogram bin for a measured breath rate is determined 632. Each of the concurrently running histograms is updated 641-645 based on the measured breath rate. In some implementations, the breath rates may be computed in breaths/minute and the spacing of the histogram bins is 1 breath/minute. After an aperture is concluded 651-655, the median rate value for the aperture is computed 661-665. If an insufficient number of breaths are detected during an aperture, e.g., fewer than 100 breaths, then the aperture may be labeled invalid and a median for that aperture may not be computed. Throughout the 24 hour period, the running maximum of the median rate values for the 10 minute apertures is retained 671 and the running minimum of the median rate values for the 30 minute apertures is retained 672. After the 24 hour period is concluded 681, 682, the daily maximum rate is reported 691, and the daily minimum rate is reported 692. The daily median respiration rate is determined 665 as the median rate value of the 24 hour aperture and reported 693. The daily maximum, minimum, and median values may be stored, telemetered to a remote device, displayed on a display, or otherwise accessed by a physician or others. The daily minimum, maximum and median rates may be numerically displayed. A respiration rate trend of one or more of the minimum, maximum, or median rates may be developed that spans a number of days and may also be displayed.

Various embodiments described herein may be used in connection with devices that provide for CHF monitoring, diagnosis, and/or therapy. A respiration sensing medical device (RSMD) of the present invention may provide CHF therapy features involving dual-chamber or bi-ventricular pacing/therapy, cardiac resynchronization therapy, cardiac function optimization, drug therapy, respiration therapy and/or other CHF related methodologies. For example, an RSMD of the present invention may incorporate features of one or more of the following references: commonly owned U.S. patent application Ser. No. 10/270,035, filed Oct. 11, 2002, entitled "Timing Cycles for Synchronized Multisite Cardiac Pacing;" and U.S. Pat. Nos. 6,411,848; 6,285,907; 4,928,688; 6,459,929; 5,334,222; 6,026,320; 6,371,922; 6,597,951; 6,424,865; and 6,542,775, each of which is hereby incorporated herein by reference.

The respiration metrics and/or trends developed as described in various embodiments herein may be used in a number of ways to assist in the diagnosis and/or treatment of patients suffering from CHF or other respiratory or cardiopulmonary disorders. According to one aspect of the invention, the respiration information may be presented to a patient's physician for use in making diagnosis and/or therapy decisions. In one implementation, respiration information acquired by the RSMD, e.g., respiration characteristics (estimated or measured values), respiration metrics, and/or trends of respiration characteristics and/or metrics, may be presented for viewing on demand by the physician via a display on a device programmer or other remote device. The physician may use the respiration information to diagnose the patient and/or to initiate, terminate or modify therapy delivered to the patient. In some implementations, an implantable RSMD may communicate wirelessly with a remote device to download respiration information periodically so that current respiration information is available to the physician.

According to another aspect, the respiration information may be used by the RSMD to automatically make a diagnosis or to automatically control therapy. The RSMD may compare the respiration metrics and/or trends developed as described in the various embodiments, to one or more thresholds. The RSMD may detect or diagnose the presence of a disease/disorder, may determine the progression or regression of disease/disorder symptoms, and/or may determine if therapy should be modified based on the comparison. The respiration information may be used alone, or may be combined with other information related to the disease/disorder of concern. For example, the respiration information may be used in conjunction with additional sensed information and may also be used in conjunction with patient historical information or patient input information, such as patient weight, or drug use information.

In one implementation, the RSMD may acquire information related to patient posture, cardiac functioning, and/or patient activity along with developing the respiration metrics and/or trends described herein. The RSMD may use the acquired posture, cardiac and/or activity information in combination with the respiration metrics and/or trends to enhance diagnosis or therapy. For example, the RSMD may compare patient posture, cardiac functioning, activity, and respiration rate, respectively, to thresholds associated with each of these variables. In another example, the RSMD may combine the posture, cardiac functioning, activity and respiration information via a weighted sum, for example. The combined information may be compared to a single threshold to facilitate diagnosis and/or to determine the progression of disease symptoms and/or to indicate if therapy modification is appropriate.

If the RSMD automatically generates a diagnosis, the diagnosis may be provided on demand, or in the form of an automatic alert generated when patient conditions indicate that the patient symptoms have deteriorated beyond a trigger level. If the RSMD automatically initiates, terminates, or modifies therapy, the RSMD may develop a control signal transmitted to one or more therapy devices indicating the therapy change. The control signal may be generated by the RSMD based on the respiration information and/or additional information. For example, if the RSMD is used in conjunction with a CRM device, the control signal may control modification of various pacing parameters. In such an implementation, the therapy modification may include changing the pacing mode, e.g., switching pacing from single ventricular pacing to bi-ventricular pacing, changing the pacing site, changing pacing rate, and/or modifying various pacing delays such as the atrioventricular pacing delay and/or the interventricular pacing delay. In another example, if the RSMD is used in conjunction with an implantable drug delivery device, such as a drug pump, the RSMD may automatically modify the type and/or titration of drugs used to treat the patient's disease/disorder. Alternatively, the RSMD may inform the patient that their medication should be changed. The automatic therapy modification may be remotely reviewed and approved by the patient's physician prior to making or suggesting the modification.

Certain configurations illustrated herein are generally described as capable of implementing various functions traditionally performed by an implantable cardioverter/defibrillator (ICD), and may operate in numerous cardioversion/defibrillation modes as are known in the art. Examples of ICD circuitry, structures and functionality, aspects of which may be used in a RSMD of the present invention, are disclosed in commonly owned U.S. Pat. Nos. 5,133,353; 5,179,945; 5,314,459; 5,318,597; 5,620,466; and 5,662,688, which are hereby incorporated herein by reference.

In particular configurations, systems and methods may perform functions traditionally performed by pacemakers, such as providing various pacing therapies as are known in the art, in addition to cardioversion/defibrillation therapies. Examples of pacemaker circuitry, structures and functionality, aspects of which may be incorporated in a RSMD of the present invention, are disclosed in commonly owned U.S. Pat. Nos. 4,562,841; 5,284,136; 5,376,106; 5,036,849; 5,540,727; 5,836,987; 6,044,298; and 6,055,454, which are hereby incorporated herein by reference. It is understood that RSMD configurations may provide for non-physiologic pacing support in addition to, or to the exclusion of, bradycardia and/or anti-tachycardia pacing therapies.

A RSMD in accordance with the present invention may implement diagnostic and/or monitoring functions as well as provide cardiac stimulation therapy. Examples of cardiac monitoring circuitry, structures and functionality, aspects of which may be incorporated in a RSMD of the present invention, are disclosed in commonly owned U.S. Pat. Nos. 5,313,953; 5,388,578; and 5,411,031, which are hereby incorporated herein by reference.

Figure 7:
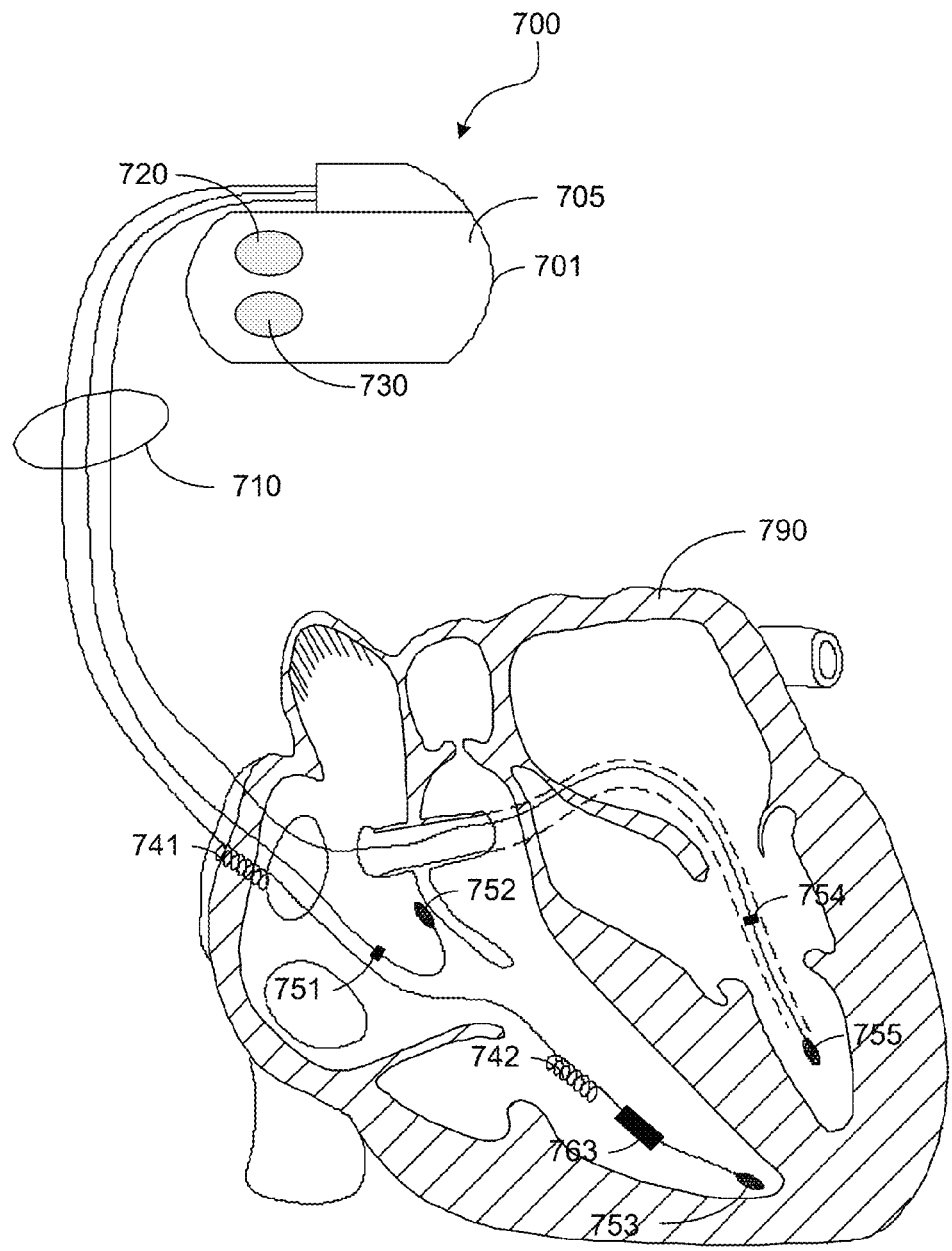
FIG. 7 illustrates a medical device configured to estimate characteristics of a respiration signal and/or develop respiration metrics and trends in accordance with embodiments of the present invention.

Referring now to FIG. 7, there is illustrated an embodiment of a medical device configured to estimate characteristics of a respiration signal and/or develop respiration metrics and trends in accordance with embodiments of the present invention. In this illustrative example, the medical device comprises a cardiac rhythm management (CRM) device 700 including an implantable pulse generator 705 electrically and physically coupled to an intracardiac lead system 710.

Portions of the intracardiac lead system 710 are inserted into the patient's heart 790. The intracardiac lead system 710 includes one or more electrodes and/or sensors configured to sense electrical cardiac activity of the heart, deliver electrical stimulation to the heart, sense transthoracic impedance, sense blood (internal filling) pressure, flow, and/or temperature, sense acceleration and/or body acoustics, and/or sense other physiological parameters of interest. Portions of the housing 701 of the pulse generator 705 may optionally serve as a can electrode.

Communications circuitry is disposed within the housing 701 for facilitating communication between the pulse generator 705 and an external communication device, such as a portable or bed-side communication station, patient-carried/worn communication station (e.g., communicator), external programmer or advanced patient management system interface, for example. The communications circuitry may also facilitate unidirectional or bidirectional communication with one or more implanted, external, cutaneous, or subcutaneous physiologic or non-physiologic sensors, patient-input devices and/or information systems.

The pulse generator 705 may optionally incorporate a motion detector 720 that may be used to sense patient activity as well as various respiration and cardiac related conditions. For example, the motion detector 720 may be optionally configured to sense snoring, activity level, and/or chest wall movements associated with respiratory effort, for example. The motion detector 720 may be implemented as an accelerometer positioned in or on the housing 701 of the pulse generator 705. For a motion sensor implemented as an accelerometer, the motion sensor may also provide respiratory, e.g. rales, coughing, and cardiac, e.g. S1-S4 heart sounds, murmurs, and other acoustic information. An accelerometer may be used to sense patient activity information which may be used in conjunction with respiration information.

The lead system 710 and pulse generator 705 of the CRM 700 may incorporate one or more transthoracic impedance sensors that may be used to acquire the patient's respiration waveform, or other respiration-related information. The transthoracic impedance sensor may include, for example, one or more intracardiac electrodes 741, 742, 751-755, 763 positioned in one or more chambers of the heart 790. The intracardiac electrodes 741, 742, 751-755, 763 may be coupled to impedance drive/sense circuitry 730 positioned within the housing of the pulse generator 705.

In one implementation, impedance drive/sense circuitry 730 generates a current that flows through the tissue between an impedance drive electrode 751 and a can electrode on the housing 701 of the pulse generator 705. The voltage at an impedance sense electrode 752 relative to the can electrode changes as the patient's transthoracic impedance changes. The voltage signal developed between the impedance sense electrode 752 and the can electrode is detected by the impedance sense circuitry 730. Other locations and/or combinations of impedance sense and drive electrodes are also possible.

The lead system 710 may include one or more cardiac pace/sense electrodes 751-755 positioned in, on, or about one or more heart chambers for sensing electrical signals from the patient's heart 790 and/or delivering pacing pulses to the heart 790. The intracardiac sense/pace electrodes 751-755, such as those illustrated in FIG. 7, may be used to sense and/or pace one or more chambers of the heart, including the left ventricle, the right ventricle, the left atrium and/or the right atrium. The lead system 710 may include one or more defibrillation electrodes 741, 742 for delivering defibrillation/cardioversion shocks to the heart.

The lead system 710 may include one or more leads each having one or more electrodes that extend into the heart. FIG. 7 shows three such leads, one that extends into the right atrium, one that extends into the right ventricle, and one that extends into a coronary vein for placement at the surface of the left ventricle. The left ventricular lead, in particular, includes an LV distal electrode 755 and an LV proximal electrode 754 located at appropriate locations in or about the left ventricle for pacing and/or sensing the left ventricle. The left ventricular lead may be guided into the right atrium of the heart via the superior vena cava. From the right atrium, the left ventricular lead may be deployed into the coronary sinus ostium, the opening of the coronary sinus. The lead may be guided through the coronary sinus to a coronary vein of the left ventricle. This vein is used as an access pathway for leads to reach the surfaces of the left ventricle that are not directly accessible from the right side of the heart.

The pulse generator 705 may include circuitry for detecting cardiac arrhythmias and/or for controlling pacing or defibrillation therapy in the form of electrical stimulation pulses or shocks delivered to the heart through the lead system 710. The pulse generator 705 may also incorporate circuitry, structures and functionality of the implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243; 6,360,127; 6,597,951; and US Patent Publication No. 2002/0143264, which are hereby incorporated herein by reference.

For purposes of illustration, and not of limitation, various embodiments of devices implemented in accordance with the present invention are described herein in the context of RSMDs that may be implanted under the skin in the chest region of a patient. An RSMD may, for example, be implanted subcutaneously such that all or selected elements of the device are positioned on the patient's front, back, side, or other body locations suitable for sensing cardiac activity and/or delivering cardiac stimulation therapy. It is understood that elements of the RSMD may be located at several different body locations, such as in the chest, abdominal, or subclavian region with electrode elements respectively positioned at different regions near, around, in, or on the heart.

The primary housing (e.g., the active or non-active can) of the RSMD, for example, may be configured for positioning outside of the rib cage at an intercostal or subcostal location, within the abdomen, or in the upper chest region (e.g., subclavian location, such as above the third rib). In one implementation, one or more leads incorporating electrodes may be located in direct contact with the heart, great vessel or coronary vasculature, such as via one or more leads implanted by use of conventional transvenous delivery approaches. In another implementation, one or more electrodes may be located on the primary housing and/or at other locations about, but not in direct contact with the heart, great vessel or coronary vasculature.

In a further implementation, for example, one or more electrode subsystems or electrode arrays may be used to sense cardiac activity and deliver cardiac stimulation energy in a RSMD configuration employing an active can or a configuration employing a non-active can. Electrodes may be situated at anterior and/or posterior locations relative to the heart. Examples of useful electrode locations and features that may be employed in various embodiments of the present invention are described in commonly owned, co-pending U.S. patent application Ser. Nos. 10/465,520 filed Jun. 19, 2003, entitled "Methods and Systems Involving Subcutaneous Electrode Positioning Relative to a Heart," and 10/738,608 filed Dec. 17, 2003, entitled "Noise Canceling Cardiac Electrodes," which are hereby incorporated herein by reference.

Figure 8:
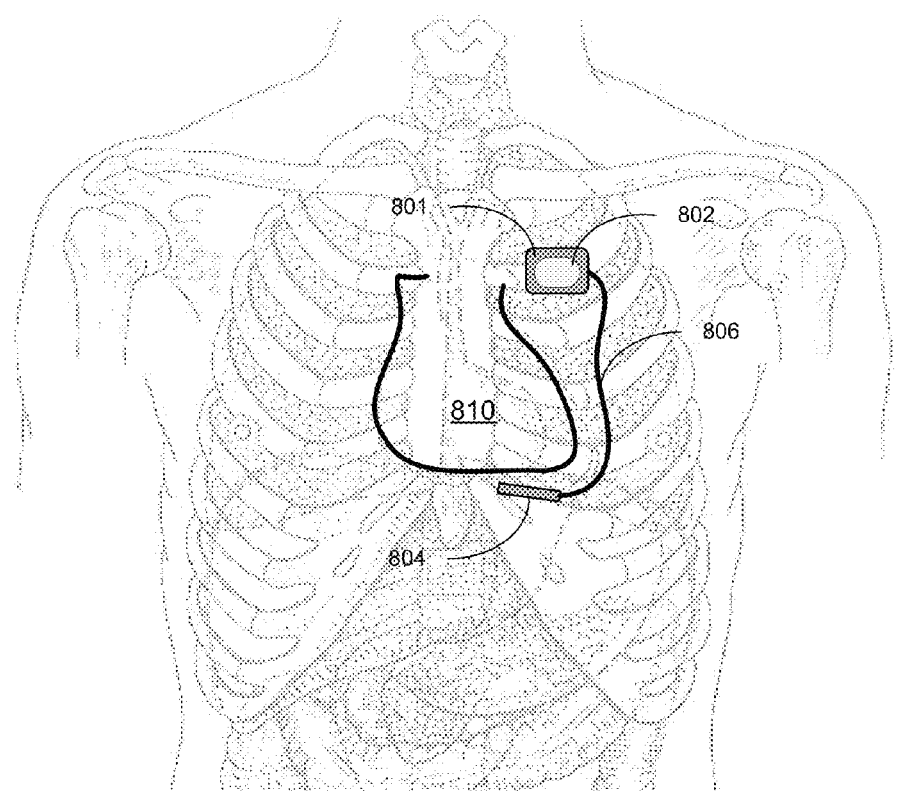
FIG. 8 is an illustration of an implantable medical device including a subcutaneous, non-intrathoracic lead assembly shown implanted outside the ribcage, the implantable medical device implemented to sense respiration of a patient for use in determining respiration metrics in accordance with embodiments of the invention.

In one configuration, as is illustrated in FIG. 8, electrode subsystems of a RSMD system are arranged about a patient's heart 810. The RSMD system includes a first electrode subsystem, comprising a can electrode 802, and a second electrode subsystem 804 that includes at least two electrodes or at least one multi-element electrode. The second electrode subsystem 804 may include a number of electrodes used for sensing and/or electrical stimulation.

In various configurations, the second electrode subsystem 804 may include a combination of electrodes. The combination of electrodes of the second electrode subsystem 804 may include coil electrodes, tip electrodes, ring electrodes, multi-element coils, spiral coils, spiral coils mounted on non-conductive backing, screen patch electrodes, and other electrode configurations as will be described below. A suitable non-conductive backing material is silicone rubber, for example.

The can electrode 802 is positioned on the housing 801 that encloses the RSMD electronics. The RSMD system shown in FIG. 8 incorporates one or more sensors configured to sense respiration. A sensing element, e.g., electrode, used for respiration sensing may be disposed on housing 801, such that element 802 may be representative of such electrode(s) alone or in combination with a can electrode. Sensing elements used for respiration sensing may be disposed on another component of the RSMD system, such as on lead 806, a lead separate from lead 806, or on the subsystem element 804, which may be representative of such sensing element(s) alone or in combination with a cardiac electrode.

A RSMD of the present invention may be implemented to communicate with a patient management server or network via an appropriate communications interface or an external programmer. A RSMD of the present invention may be used within the structure of an APM system. The advanced patient management system allows physicians to remotely and automatically monitor cardiac and respiratory functions, as well as other patient conditions.

In one example, a RSMD implemented as a cardiac pacemaker, defibrillator, or resynchronization device may be equipped with various telecommunications and information technologies that enable real-time data collection, diagnosis, and treatment of the patient. Various RSMD embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

The components, functionality, and structural configurations depicted herein are intended to provide an understanding of various features and combination of features that may be incorporated in a RSMD. It is understood that a wide variety of RSMDs and other implantable cardiac monitoring and/or stimulation device configurations are contemplated, ranging from relatively sophisticated to relatively simple designs. As such, particular RSMD or cardiac monitoring and/or stimulation device configurations may include particular features as described herein, while other such device configurations may exclude particular features described herein.

Figure 9:
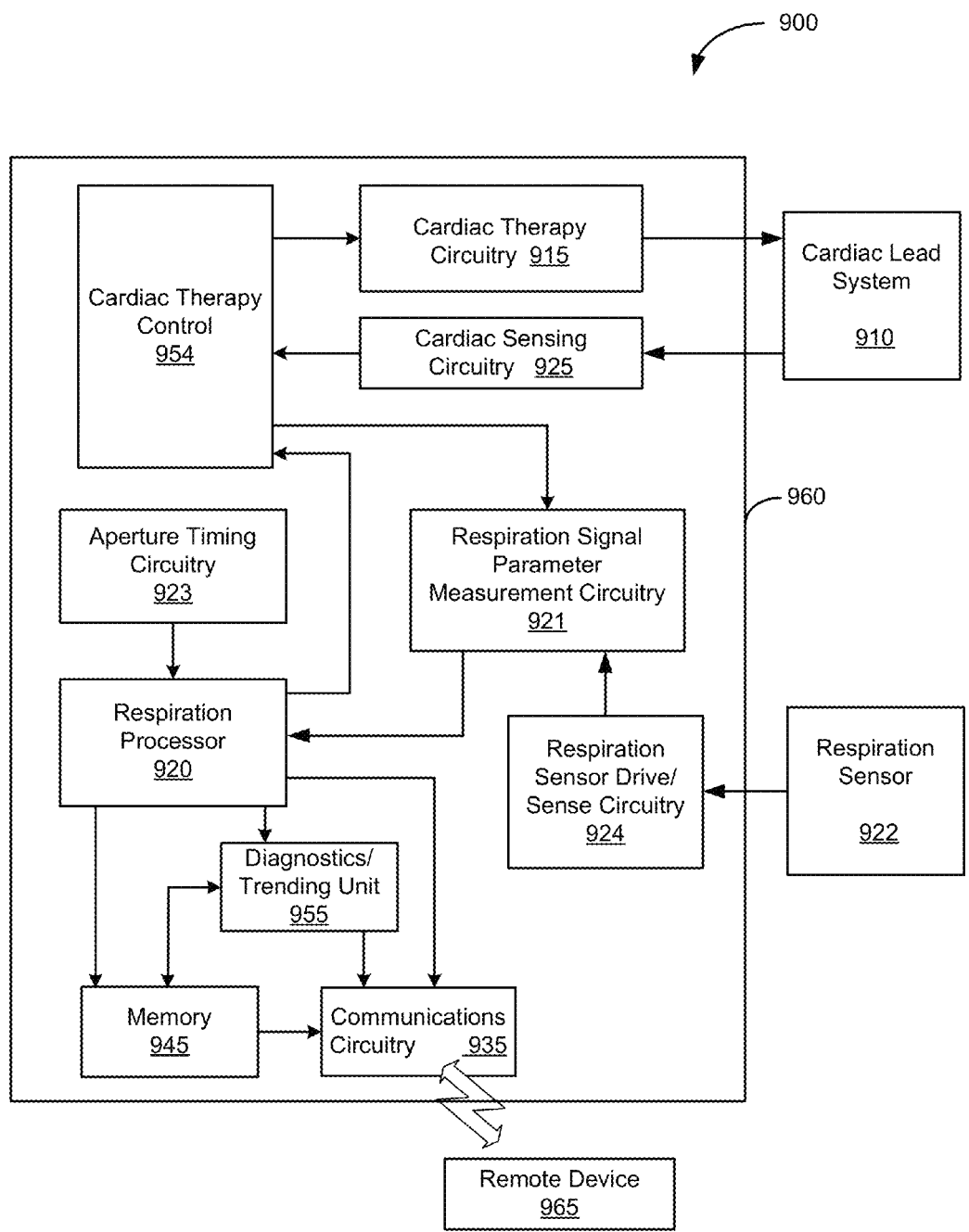
FIG. 9 is a block diagram showing a variety of illustrative operations that may be performed based on measuring and/or estimating respiration characteristics that may be used to develop respiration metrics or trends in accordance with embodiments of the invention.

FIG. 9 illustrates a block diagram of a system 900 suitable for implementing the methods of the invention as illustrated, for example, by the processes of FIGS. 1-6. In some embodiments, circuitry for estimating characteristics of patient respiration, determining respiration metrics and/or developing respiration trends is disposed within the housing of an implantable cardiac rhythm device 960. The cardiac rhythm device 960 includes a cardiac lead system 910 that is electrically coupled to the patient's heart. Electrical signals from the patient's heart are sensed via the lead system 910 by cardiac sensing circuitry 925. The cardiac therapy control circuitry 954 may detect arrhythmic conditions, such as bradyarrhythmia or tachyarrhythmia, based on the sensed cardiac electrical signals. Cardiac therapy control circuitry 954 controls cardiac therapy circuitry 915 which generates electrical stimulation pulses delivered to the heart via the lead system 910 to treat various heart rhythm irregularities. For example, the cardiac therapy circuitry 914 may generate a series of low energy electrical pacing pulses timed to assist the heart in maintaining a hemodynamically appropriate rhythm. The cardiac therapy circuitry 914 may generate high energy shocks delivered to the heart if the cardiac control circuitry 954 detects tachycardia or fibrillation, arrhythmic conditions producing a heart rate that is too fast and possibly lethal.

The system 900 includes a sensor 922 for sensing patient respiration. The sensor may be configured, for example, as intracardiac electrodes used to develop a transthoracic impedance signal which tracks respiration. Respiration sensor drive circuitry 924 provides the necessary drive signals to activate the drive electrodes 922. Response signals are sensed via sense electrodes 922 and are conditioned by the respiration sense circuitry 924.

The respiration drive/sense circuitry 924 generates a respiration signal that is received by the respiration characteristic measurement circuitry 921. The measurement circuitry 921 measures one or more characteristics of the respiration signal. In various embodiments, the characteristic measured may comprise, for example, breath rate, breath interval, tidal volume, or other respiration characteristics. A respiration characteristic may be measured for each breath cycle, e.g., breath rate per cycle or breath interval duration per cycle, or multiple breath cycles may be used in the respiration characteristic measurement, e.g., average tidal volume for X number of breath cycles.

The measurement circuitry 921 may pre-process the respiration signal received from the respiration drive/sense circuitry 924 to remove spurious breath detections, for example, as described in connection with FIGS. 4 and 5. In one scenario, the cardiac therapy control processor 954 provides R-R interval information to the measurement circuitry 921. The measurement circuitry 921 compares breath intervals to filtered R-R interval estimates to identify and remove erroneous breath detections that are due to cardiac activity as previously described.

A respiration processor 920 receives the measurements and uses the measurements to estimate characteristics of the patient respiration. The patient respiration characteristics are estimated with respect to apertures timed by the aperture timing circuitry 923. For example, in one implementation, the measurement circuitry 921 measures a respiration rate for each breath cycle. The respiration processor 920 estimates a characteristic of the patient respiration for each aperture. In some embodiments, the respiration processor 920 may form a histogram of measured respiration rates received from the measurement circuitry 921 and estimate the respiration rate of the aperture as the median respiration rate determined from the aperture histogram. The respiration rates for each aperture may be stored in memory 945, or may be transmitted via communications circuitry 935 to a remote device 965.

The respiration processor 920 may estimate respiration characteristics for consecutive and/or overlapping apertures. In some implementations, aperture durations may be selected based on the particular respiration characteristic being estimated. Respiration characteristic estimates of the apertures may be used to determine respiration metrics associated with a number of apertures spanning a period of time. For example, daily minimum and maximum respiration rates, or other daily metrics may be determined for apertures spanning a 24 hour period. The respiration processor, in conjunction with the memory, may form a trend of the measured respiration characteristics, the respiration characteristic estimates, the respiration metrics, and/or other respiration information. The respiration metrics and/or trends developed by the respiration processor 920 may be used by a diagnostics unit 955 to track the presence and/or progression of a disease, such as heart failure. The respiration metrics and/or trends developed by the respiration processor 920 may be transmitted to a remote device 965 via the communications circuitry 935. The respiration processor 920 may generate a control signal to control the cardiac therapy. For example, the cardiac therapy control unit 954 may modify a pacing therapy delivered to the patient based on the control signal generated by the respiration processor.

A system according to the present invention may include one or more of the features, structures, methods, or combinations thereof described herein. For example, a cardiac monitor, cardiac stimulator, drug pump, or other type of implantable, partially implantable or patient-external medical device may be implemented to include one or more of the advantageous features and/or processes described above. It is intended that such an implanted, partially implanted or patient external device need not include all of the features described herein, but may be implemented to include selected features that provide for useful structures and/or functionality. Such a device may be implemented to provide a variety of therapeutic or diagnostic functions.

The implementation described in connection with FIG. 9 presumes that measurement of respiration characteristics, estimation of respiration characteristics, determination of respiration metrics and developing respiration trends is performed within an implantable device. In other configurations, these processes may be performed by the remote device 965, which may comprise a patient-external device, or by two or more implantable or patient-external devices that are communicatively coupled. For example, in one configuration, the implantable device 960 may perform one subset of the functions described above and the remote device 965, which may be a device programmer or advanced patient management system, may perform another subset of the functions.

Various modifications and additions can be made to the preferred embodiments discussed hereinabove without departing from the scope of the present invention. For example, the methods and systems described herein generally include an implantable device or sensor for sensing respiratory characteristics and/or computing a patient's respiration rate and/or respiration rate distribution. It is understood that methods and systems of the present invention may be implemented using patient-external devices and sensors, and that the embodiments described herein may be implemented in the context of such patient-external devices and sensors. Accordingly, the scope of the present invention should not be limited by the particular embodiments described above, but should be defined only by the claims set forth below and equivalents thereof.

What is claimed is:

1. A method of determining one or more respiration metrics, comprising:
   generating a signal indicative of respiration of a patient using one or more sensors;
   receiving the signal indicative of respiration in an implantable device and determining, for each aperture of a plurality of shorter time apertures and for each aperture of a plurality of longer time apertures, an estimated characteristic of the respiration of the patient based on the respiration signal; and
   the implantable device determining one or more respiration metrics using one or both of the estimated respiration characteristics of the plurality of shorter time apertures and the estimated respiration characteristics of the plurality of longer time apertures, wherein determining the one or more respiration metrics includes determining a maximum respiration metric based on the estimated characteristics for each of the plurality of shorter time apertures and determining a minimum respiration metric based on the estimated characteristics of each of the plurality of longer time apertures.

2. The method of claim 1, wherein determining the estimated respiration characteristic for each aperture comprises:
   measuring a respiration characteristic for each breath cycle of the aperture; and
   determining the estimated respiration characteristic for the aperture based on the measured respiration characteristics.

3. The method of claim 2, wherein determining the estimated respiration characteristic for the aperture comprises determining the estimated respiration characteristic based on a median value of the measured respiration characteristics.

4. The method of claim 1, wherein determining the estimated respiration characteristic for each aperture comprises determining an estimated respiration rate for each aperture.

5. The method of claim 1, wherein at least one of generating the signal, determining the estimated characteristic, and determining the one or more respiration metrics is performed at least in part by the implantable device.

6. The method of claim 1, wherein:
   determining the estimated respiration characteristic for each of the plurality of shorter time apertures comprises determining a maximum respiration rate for each of the plurality of shorter time apertures;
   determining the estimated respiration characteristic for each of the plurality of longer time apertures comprises determining a minimum respiration rate for each of the plurality of longer time apertures; and
   determining the respiration metrics comprises determining a daily maximum respiration rate using the maximum respiration rates of the plurality of shorter time apertures and determining a daily minimum respiration rate using the minimum respiration rates of the plurality of longer time apertures.

7. The method of claim 1, further comprising developing a trend using at least one of the estimated respiration characteristics determined for the plurality of shorter time apertures, the estimated respiration characteristics determined for the plurality of longer time apertures, and the one or more respiration metrics.

8. The method of claim 1, further comprising detecting a presence of a disease or disorder using at least one of the estimated respiration characteristics determined for the plurality of shorter time apertures, the estimated respiration characteristics determined for the plurality of longer time apertures, and the one or more respiration metrics.

9. The method of claim 1, further comprising tracking progression of heart failure using at least one of the estimated respiration characteristics determined for the plurality of shorter time apertures, the estimated respiration characteristics determined for the plurality of longer time apertures, and the one or more respiration metrics.

10. The method of claim 9, further comprising initiating, modifying or terminating therapy based on the heart failure progression.

11. The method of claim 10, wherein the therapy includes a cardiac pacing therapy.

12. The method of claim 1, wherein at least some of the plurality of shorter time apertures overlap each other.

13. The method of claim 1, wherein at least some of the plurality of longer time apertures overlap each other.

14. A method, comprising:
   generating a signal indicative of respiration of a patient using one or more sensors;
   receiving the signal indicative of respiration in an implantable device;
   the implantable device determining, for each aperture of a plurality of shorter time apertures and for each aperture of a plurality of longer time apertures, an estimated characteristic of the respiration based on the respiration signal;

the implantable device determining one or more respiration metrics using one or both of the estimated respiration characteristics of the plurality of shorter time apertures and the estimated respiration characteristics of the plurality of longer time apertures, wherein determining the one or more respiration metrics includes determining a maximum respiration metric based on the estimated characteristics for each of the plurality of shorter time apertures and determining a minimum respiration metric based on the estimated characteristics of each of the plurality of longer time apertures;

the implantable device identifying spurious respiration cycles associated with cardiac activity; and the implantable device excluding the spurious respiration cycles when determining the estimated respiration characteristic.

15. The method of claim 14, wherein determining the estimated respiration characteristic for each aperture comprises determining an estimated respiration rate for each aperture.

16. The method of claim 14, wherein:

determining the estimated respiration characteristic for each of the plurality of shorter time apertures comprises determining a maximum respiration rate for each of the plurality of shorter time apertures;

determining the estimated respiration characteristic for each of the plurality of longer time apertures comprises determining a minimum respiration rate for each of the plurality of longer time apertures; and determining the respiration metrics comprises determining a daily maximum respiration rate using the maximum respiration rates of the plurality of shorter time apertures and determining a daily minimum respiration rate using the minimum respiration rates of the plurality of longer time apertures.

17. A method, comprising:

generating a signal indicative of respiration of a patient using one or more sensors;

receiving the signal indicative of respiration in an implantable device and determining, for each aperture of a plurality of shorter time apertures and for each aperture of a plurality of longer time apertures, an estimated characteristic of the respiration based on the respiration signal; and the implantable device determining one or more respiration metrics using one or both of the estimated respiration characteristics of the plurality of shorter time apertures and the estimated respiration characteristics of the plurality of longer time apertures, wherein determining the one or more respiration metrics includes determining a maximum respiration metric based on the estimated characteristics for each of the plurality of shorter time apertures and determining a minimum respiration metric based on the estimated characteristics of each of the plurality of longer time apertures and wherein at least some of the plurality of shorter time apertures overlap each other and at least some of the plurality of longer time apertures overlap each other.

18. The method of claim 17, wherein:

determining the estimated respiration characteristic for each of the plurality of shorter time apertures comprises determining a maximum respiration rate for each of the plurality of shorter time apertures;

determining the estimated respiration characteristic for each of the plurality of longer time apertures comprises determining a minimum respiration rate for each of the plurality of longer time apertures; and determining the respiration metrics comprises determining a daily maximum respiration rate using the maximum respiration rates of the plurality of shorter time apertures and determining a daily minimum respiration rate using the minimum respiration rates of the plurality of longer time apertures.

19. A method of determining one or more respiration metrics, comprising:

generating a signal indicative of respiration of a patient using one or more sensors;

receiving the signal indicative of respiration in an implantable device and determining, for each aperture of a plurality of shorter time apertures and for each aperture of a plurality of longer time apertures, an estimated characteristic of the respiration based on the respiration signal;

the implantable device determining one or more respiration metrics using one or both of the estimated respiration characteristics of the plurality of shorter time apertures and the estimated respiration characteristics of the plurality of longer time apertures, wherein the estimated respiration characteristic of each shorter time aperture includes a median value of respiration rates measured during the shorter time aperture and the estimated respiration characteristic of each longer time aperture includes a median value of respiration rates measured during the longer time aperture and wherein determining the respiration metrics includes determining a maximum of the median values of the respiration rates measured for each of the plurality of shorter time apertures and determining a minimum of the median values of the respiration rates measured for each of the plurality of longer time apertures.

20. The method of claim 19, further comprising:

determining a daily maximum respiration rate using the maximum of the median values of the respiration rates for each of the plurality of shorter time apertures and determining a daily minimum respiration rate using the minimum of the median values of the respiration rates for each of the plurality of longer time apertures.

* * * * *